US006268200B1

(12) United States Patent
Tucker et al.

(10) Patent No.: US 6,268,200 B1
(45) Date of Patent: Jul. 31, 2001

(54) BIOTHERAPEUTIC VIRUS ATTENUATION USING VARIABLE FREQUENCY MICROWAVE ENERGY

(75) Inventors: Denise A. Tucker, Raleigh; Roger Lauren Lundblad, Chapel Hill; Howard M. Reisner, Durham, all of NC (US); Henry Shannon Kingdon, Lake Forest, IL (US)

(73) Assignees: Lambda Technologies, Inc., Morrisville, NC (US); Baxter International, Inc., Deerfield, IL (US)

( * ) Notice: Subject to any disclaimer, the term of this patent is extended or adjusted under 35 U.S.C. 154(b) by 0 days.

(21) Appl. No.: 09/232,503

(22) Filed: Jan. 15, 1999

(51) Int. Cl.$^7$ .................................................. C12N 7/04

(52) U.S. Cl. ............................... 435/236; 435/1.1; 435/2; 435/173; 435/235.1; 422/21

(58) Field of Search ............................. 435/235.1, 236, 435/173, 1.1, 2; 422/21

(56) References Cited

U.S. PATENT DOCUMENTS

| | | |
|---|---|---|
| 3,660,234 | 5/1972 | Gray . |
| 3,753,651 | * 8/1973 | Boucher . |
| 3,926,556 | * 12/1975 | Boucher . |
| 4,188,375 | 2/1980 | Straub . |
| 4,250,139 | 2/1981 | Luck et al. . |
| 4,839,142 | 6/1989 | Charm . |
| 4,861,956 | * 8/1989 | Courneya . |
| 4,880,512 | 11/1989 | Cornelius et al. . |
| 4,975,246 | 12/1990 | Charm . |
| 5,073,167 | 12/1991 | Carr et al. . |
| 5,539,673 | 7/1996 | Charm et al. . |

FOREIGN PATENT DOCUMENTS

| | | | |
|---|---|---|---|
| 0 217 662 B1 | 1/1994 | (EP) . | |
| WO 96/09843 | 4/1996 | (WO) . | |
| WO 98/57523 | 12/1998 | (WO) | ............................. H05B/6/64 |

OTHER PUBLICATIONS (Abstract) Szmigielski et al., In vitro and in vivo inhibition of virus multiplication by microwave hyperthermia The Excerpta Medica Database No. 78039052, Archives of Virology, vol. 53, No. 1–2, pp. 71–77 (1977).
Kohli et al., Calculated Microwave Absorption of Double-Helical B–Conformation Poly (dG) Poly (dC), Biopolymers, vol. 20, pp. 853–864 (1981).
(Abstract) Sanborn et al., Microwave sterilization of plastic tissue culture vessels for reuse—tested against 9 bacterial cultures including Bacillus also polio and parainfluenza virus and phage, Dialog Select, Appl.Environ.Microbiol. 44, pp. 960–964 (1982).
Van Zandt et al., Communications to the Editor, Absorption of Microwave Radiation by DNA Double Heliz in aquo, Biopolymers, vol. 21, pp. 1465–1468 (1982).
Swicord et al., Microwave Absorption of DNA Between 8 and 12 GHz, Biopolymers, vol. 21, pp. 2453–2460 (1982).
(Abstract) Vasl et al., Virus behavior in irradiated sludge, EMBASE No. 83220032, Water Sci. Technol. 15/5, pp. 123–127 (1983).
Hakim et al., The Speed of Sound in DNA, Biopolymers, vol. 23, pp. 1185–1192 (1984).
de Xammar Oro et al., Dielectric Properties of Aqueous Solutions of Sonicated DNA above 40 MHz, Biopolymers, vol. 23, pp. 1457–1463 (1984).
Edwards, Microwave–Field Driven Acoustic Modes in Selected DNA Molecules, Dissertation, Graduate School of the University of Maryland (1984).
Bonincontro et al., Effect of Ions on Counterion Fluctuation in Low–Molecular Weight DNA Dielectric Dispersions, Biophysical Society, vol. 45, pp. 495–501 (Mar. 1984).
Takashima et al., Dielectric Behavior of DNA Solution at Radio and Microwave Frequencies (at 20° C), Biophysical Society, vol. 46, pp. 29–34 (Jul. 1984).
(Abstract) K. Buckle, A Study of the Effects of Microwave Energy on Plant Viruses, Dialog Select, Trans. Kans. Acad. Sci., 88 (3–4), pp. 138–143 (1985).
Horowitz et al., Inactivation of viruses in labile blood derivatives, Transfusion, vol. 25, No. 6, pp. 523–527 (1985).
Edwards et al., Microwave Field Driven Acoustic Modes in DNA, Biophysical Society, vol. 47, pp. 799–807 (Jun. 1985).
Davis et al., Direct Excitation of Internal Modes of DNA by Microwaves, Bioelectrochemistry & Biomagnetic, vol. 16, pp. 63–76 (1986).
Sagripanti et al., Rapid communication, DNA structural changes caused by microwave radiation, Int. J. Radiat. Biol. vol. 50, No. 1, pp. 47–50 (1986).
Bonincontro et al., Temperature Dependence of Dielectric Constant at 10 GHz of Na–DNA Gels, Biopolymers, vol. 25, pp. 241–247 (1986).
Sagripanti et al., Microwave Effects on Plasmid DNA, Radiation Research 110, pp. 219–231 (1987).
Tao et al., The Dynamics of the DNA Hydration Shell at Gigahertz Frequencies, Biopolymers, vol. 26, pp. 171–188 (1987).

(List continued on next page.)

Primary Examiner—Leon B. Lankford, Jr.
(74) Attorney, Agent, or Firm—Myers Bigel Sibley & Sajovec (57) ABSTRACT

Virus attenuation is performed on a lyophilized biotherapeutic sealed within a microwave permeable container without harming the biotherapeutic and without exposing the biotherapeutic to additional viruses, by subjecting the container and biotherapeutic therewithin to variable frequency microwave energy. The container and biotherapeutic therewithin are swept with at least one range of microwave frequencies. Each range of microwave frequencies has a central frequency selected to break apart helix strands of a nucleic acid of the virus, to modify a capsid enclosing a nucleic acid of the virus, or to selectively couple to water molecules inside the capsid without harming the biotherapeutic or the container.

31 Claims, 4 Drawing Sheets

OTHER PUBLICATIONS

Gabriel et al., Microwave absorption in aqueous solutions of DNA, Nature, vol. 328, pp. 145–146 (Jul. 1987).

Foster et al., "Resonances" in the Dielectric Absorption of DNA?Biophysical Society, vol. 52, pp. 421–425 (Sep. 1987).

Kaeser, Ways to Reduced the Risk of Transmission of Viral Infections by Plasma and Plasma Products, International Forum, pp. 228–245 (1988).

Bonincontro et al., DNA–protamine interactions studied by dielectric and optical measurements, 627th Meeting, Nottingham, vol. 17 (Jun. 1988).

Gabriel et al., Dielectric behavior of aqueous solutions of plasmid DNA at microwave frequencies, Biophysical Journal, vol. 55, pp. 29–34 (Jan. 1989).

(Abstract) Mishu et al., Foodborne hepatitis A: Evidence that microwaving reduces risk?, EMBASE No. 90272041, J. Infect. Dis. 162/3 (655–658) (1990).

(Abstract) Lange et al., Japanese Encephalitis Virus JEV Potentiation of Lethality in Mice by Microwave Radiation, Dialog Select, Bioelectromagnetics, 12(6), pp. 335–348 (1991).

Pedone et al., Temperature dependence of DNA dielectric dispersion at radiofrequency, Biochimica et Biophysica Acta, pp. 580–584 (1991).

Charm et al., High–Temperature Short–Time Heat Inactivation of HIV and Other Viruses in Human Blood Plasma, Vox Sang, vol. 62, pp. 12–20 (1992).

Bernhardt, Non–ionizing radiation safety: radiofrequency radiation, electric and magnetic fields, Phys. Med. Biol., vol. 327, No. 4, pp. 807–844 (1992).

Quan et al., Effects of Microwave Radiation on Anti–infective Factors in Human Milk, Pediatrics, vol. 89 No. 4, pp. 667–669 (Apr. 1992).

Hart, H. et al., Inactivation of Viruses during Ultraviolet Light Treatment of Human Intravenous Immunoglobulin and Albumin, Vox Sang, vol. 64, pp. 82–88 (1993).

Morgenthaler, Methods for inactivation of viruses in plasma products, Biotechnology of Blood Proteins, vol. 227, pp. 221–228 (1993).

Bonincontro et al., Influence of defects on the electrophoretic, thermodynamic and dielectric properties of a 21 base pair DNA in solution, Biochimica et Biophysica Acta., 1171, pp. 288–294 (1993).

Hanson et al., Gamma Radiation and Virus Inactivation, Art to Science, vol. 12 No. 2 (Spring 1993).

Pothakamury et al., Magnetic–Field Inactivation of Microorganism and Generation of Biological Changes, Food Technology, pp. 85–93(Dec. 1993).

(Abstract) Hoffman et al., Assessment of a MicrowaveBased Clinical Waste Decontamination Unit, Dialog Select, Journal of Applied Bacteriology, vol. 77, No. 6 (DEC) pp. 607–612 (1994).

(Abstract) Liertin et al., Effects of gamma rays, ultraviolet radiation, sunlight, microwaves and electromagnetic fields on gene expression mediated by human immunodeficiency virus promoter, EMBASE No. 94328378, Radiat. Res. 140/1, pp. 91–96 (1994).

(Abstract) Kakita et al., Inactivation of Lactobacillus Bacteriophage PL–1 by microwave irradiation, Microbiol. Immunol. 39/8, pp. 571–576 (1995).

(Abstract) Kindle et al., Killing activity of microwaves in milk, EMABSE No. 96263719, J. Hosp. Infect., 33/4, pp. 273–278 (1996).

(Abstract) Taylor et al., The response of the 22A strain of scrapie agent to microwave irradiation compared with boiling, Neuropathol. Appl. Neurobiol., 22/3, pp. 256–258 (1996).

(Abstract) George, Killing activity of microwaves in milk (1), EMBASE No. 97155578, J. Hosp. Infect., 35/4, pp. 319–320 (1997).

* cited by examiner

100 SUBJECTING BIOTHERAPEUTIC IN A LIQUID STATE TO ONE OR MORE VIRUS ATTENUATION PROCEDURES

102 LYOPHILIZING BIOTHERAPEUTIC FROM LIQUID STATE TO A DRIED STATE

104 SUBJECTING DRIED BIOTHERAPEUTIC TO ONE OR MORE VIRUS ATTENUATION PROCEDURES

106 SEALING LYOPHILIZED BIOTHERAPEUTIC WITHIN CONSUMER PACKAGE

108 SUBJECTING THE CONSUMER PACKAGE AND BIOTHERAPEUTIC THEREWITHIN TO VARIABLE FREQUENCY MICROWAVE RADIATION

BIOTHERAPEUTIC VIRUS ATTENUATION USING VARIABLE FREQUENCY MICROWAVE ENERGY

FIELD OF THE INVENTION

The present invention relates generally to biotherapeutics and, more particularly, to viral attenuation in biotherapeutics.

BACKGROUND OF THE INVENTION

Biotherapy refers to the treatment of diseases with materials produced by living organisms. These materials are referred to as "biotherapeutics." Exemplary biotherapeutics can include components derived from the fractionation of blood plasma which are then administered to a patient. Factor VIII is a well known biotherapeutic for treating patients with Hemophilia A. However, because such biotherapeutics are collected from living organisms, such as humans, transgenic animals, plants or immortalized cells, there is risk of contamination by viruses and other nucleic acid-based pathogens.

A virus is any of a large group of infectious submicroscopic agents ranging from about 10 nanometers to about 250 nanometers in diameter and composed of a protein sheath surrounding a nucleic acid core. Viruses are capable of infecting animals, plants and bacteria and are characterized by a total dependence on living cells for reproduction and by a lack of independent metabolism. Exemplary viruses transmissible by biotherapeutics such as blood products include, but are not limited to, Hepatitis A; Hepatitis B; Hepatitis C; Hepatitis D; Human immunodeficiency virus; and Parvovirus.

Viral control strategies include various procedures to screen biotherapeutics or their respective source materials for viruses and to remove or attenuate viruses (both known and unknown) contained therein. Known methods for attenuating viruses include filtration, chemical treatment, heat treatment, and photodynamic treatment. Filtration involves the use of membranes having the ability to selectively remove materials from fluids based on size. The separation and capture of a virus from a biotherapeutic may be accomplished by passing the biotherapeutic in a liquid state through a membrane. A large virus (e.g., Hepatitis A) can be separated from a small protein (e.g., Antithrombin III, 68,000 M.V.) by a process referred to as nanofiltration if there is no specific interaction of the viruses with the individual therapeutic protein. Specific absorption of the biotherapeutic by the membrane materials can also preclude the use of nanofiltration.

Unfortunately, small viruses, such as Parvovirus and Hepatitis G, have sizes similar to that of certain proteins and are, therefore, difficult to separate from these proteins via filtration. For example, human Parvovirus has a diameter of about 260 angstroms and contains a nucleic acid of about 5,600 base pairs and capsid protein. Fibrinogen is a high-molecular weight plasma protein with significant molecular asymmetry which possesses a hydrodynamic size which can approach the size of Parvovirus and, thus, preclude removal by filtration. Similarly, factor VIII-von Willebrand factor complex is quite large which can make the separation from small viruses by nanofiltration difficult.

Chemical treatment of biotherapeutics involves subjecting a virus contained within a biotherapeutic to a chemical or combination of chemicals. For example, solvent/detergent may be used to disrupt the lipid envelope surrounding the nucleic acid core of viruses. Unfortunately, not all viruses are lipid enveloped. Parvovirus is an example of a virus that is not lipid enveloped. Accordingly, chemical treatment with solvent and detergent is an ineffective viral attenuation method for viruses like Parvovirus and Hepatitis A. Another disadvantage of chemical treatment is that the chemicals, or resultant derivatives thereof, generally need to be removed during the manufacturing process, or demonstrated by pre-clinical and clinical studies to be innocuous, before a biotherapeutic can be administered to a patient.

Photodynamic treatment involves the use of dyes and light. A disadvantage of photodynamic treatment is it may be difficult to find a dye that is reasonably non-toxic and that has a suitable absorption spectrum. Furthermore, as with chemical treatment, the dye and photolytic products generally need to be removed from a biotherapeutic during the manufacturing process, or demonstrated by pre-clinical and clinical studies to be innocuous, before the biotherapeutic can be administered to a patient.

Heat treatment of biotherapeutics for viral attenuation is a useful, if somewhat limited, approach to viral attenuation. Heat treatment can be advantageous over chemical treatment because there are no residual chemicals to be removed. Application of heat to a biotherapeutic in the liquid state, generally referred to as pasteurization, has been applied to albumin and plasma protein fractions with considerable success. Unfortunately, biotherapeutics are often prepared and packaged in a dry (lyophilized) state. Heat treatment for viral attenuation relies on a differential effect of heat on the virus as opposed to protein. While there is limited success with heat treatment in the solid state, there are some situations where heat may be ineffective. For example, many viruses (such as Parvovirus) can withstand rather high temperatures. The temperatures at which viruses such as Parvovirus can be attenuated may also damage or kill a biotherapeutic.

Methods for heating biological materials for various reasons with single frequency microwave energy are known. For example, U.S. Pat. No. 4,250,139 to Luck et al. discloses a method of exposing dried protein to a lethal dose of single frequency microwave radiation for a time sufficient to provide a desired degree of decontamination. U.S. Pat. No. 5,073,167 to Carr et al. discloses a method of uniformly heating liquid blood and other intravenous fluids using single frequency microwave energy.

Unfortunately, it is difficult to achieve uniform distribution of microwave energy within a microwave furnace using single frequency microwave radiation. Hot spots may develop within a microwave furnace cavity which can damage a biotherapeutic being processed. In addition, repeatability of treatment time and results may not be achievable using single frequency microwave radiation without positioning a biotherapeutic in the same position and orientation within a microwave furnace cavity.

SUMMARY OF THE INVENTION

It is, therefore, an object of the present invention to provide a viral attenuation method that produces no contamination and that can be performed on a biotherapeutic in a dry (e.g., lyophilized) state.

It is another object of the present invention to provide a viral attenuation method that can be performed on a biotherapeutic within a final packaged state without requiring additional processing or packaging steps to provide a lyophilized virus-free biotherapeutic.

It is another object of the present invention to provide a viral attenuation method that can be performed on a biotherapeutic without damaging the biotherapeutic or components thereof.

It is another object of the present invention to provide a viral attenuation method that can be used to treat large quantities of a biotherapeutic simultaneously.

It is another object of the present invention to provide a viral attenuation method that can effectively irradicate Parvovirus, Hepatitis G, Hepatitis B, and other viruses, known and unknown.

These and other objects of the present invention are provided by a method of attenuating a virus contained within a dried (e.g., lyophilized) biotherapeutic, such as a blood product, sealed within a microwave permeable container without harming the biotherapeutic and without exposing the biotherapeutic to additional viruses, by subjecting the container and biotherapeutic therewithin to variable frequency microwave energy. The container and biotherapeutic therewithin are preferably swept with at least one range of microwave frequencies. Each range of microwave frequencies has a central frequency selected to disrupt a virus without harming the biotherapeutic. Disruption may include breaking a strand of a nucleic acid helix, separating multiple strands of a nucleic acid helix, and other types of damage that may be inflicted upon a nucleic acid of a virus.

Alternatively, each range of microwave frequencies has a central frequency selected to modify a capsid enclosing a nucleic acid of the virus without harming the biotherapeutic, or to alter the relation of the capsid and enclosed nucleic acid. A selected central frequency may selectively couple with water molecules either between capsid components or associated with capsid components so as to disrupt interactions between capsid components or between capsid components and nucleic acids.

The present invention may be combined with conventional virus attenuation procedures. For example, before a biotherapeutic is lyophilized from a liquid state to a dry state, virus attenuation processes, such as filtration, chemical treatment, heat treatment, photodynamic treatment, or combinations thereof, may be performed. After a biotherapeutic is lyophilized from a liquid state to a dry state, virus attenuation via heat treatment may also be performed. After sealing the lyophilized biotherapeutic within a consumer package, or other container, the use of microwave energy ensures that the biotherapeutic is virus-free and will remain virus-free as long as it is in the container.

According to another aspect of the present invention, a lyophilized virus-contaminated biotherapeutic may be packaged within a microwave permeable consumer package. A lyophilized virus-free biotherapeutic can then be produced by subjecting the consumer package to variable frequency microwave energy to attenuate viruses contained within the biotherapeutic. Preferably, the consumer package is swept with one or more ranges of microwave frequencies. Each range of microwave frequencies has a central frequency selected to disrupt a nucleic acid of the virus without harming the biotherapeutic or the consumer package. Alternatively, each range of microwave frequencies has a central frequency selected to modify a capsid enclosing a nucleic acid of the virus or to selectively couple with water molecules inside the capsid to render the nucleic acid unstable without harming the biotherapeutic or the consumer package.

The present invention is particularly advantageous when used to attenuate viruses contained within biotherapeutics derived from human blood, fractionation of a cell culture supernatant, fractionation of a fermentation supernatant, fractionation of a cell extract, fractionation of milk from a transgenic animal, or fractionation of a plant extract. The present invention is particularly advantageous when used to treat biotherapeutics infected with deoxyribonucleic acid (DNA) and/or ribonucleic acid (RNA) containing viruses such as Parvovirus and Hepatitis A.

The present invention is directed towards a specific property of a virus that is not shared with a protein, specifically, the presence of a nucleic acid which is critical for virus functions. The present invention teaches that it is possible to apply microwave irradiation of a specific quality (i.e., variable frequency microwave irradiation) that preferentially excites nucleic acid molecules and not proteins. Thus, the present invention is markedly different from conventional techniques involving heat by convection or single frequency microwave irradiation where the object is to exploit the putative differential stability of viruses and proteins. The present invention is directed specifically to the application of variable frequency microwave energy to nucleic acids. Thus, differential stability of a biotherapeutic protein and virus is not an issue.

The present invention is advantageous because it provides a non-invasive method for attenuating many types of viruses, whether known or unknown, that exist within lyophilized biotherapeutics. Because microwave energy is applied to a biotherapeutic sealed within a consumer package, such as a glass vial, the biotherapeutic cannot become contaminated by another pathogen. The present invention is particularly suited for the attenuation of small, robust viral species, such as Parvovirus, that are traditionally difficult to attenuate by conventional methods. Furthermore, the present invention is particularly suitable for large scale biotherapeutic production. Large numbers of containers or consumer packages containing biotherapeutics can be simultaneously subjected to microwave energy according to the present invention.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 1 schematically illustrates operations for attenuating viruses contained within biotherapeutics, according to the present invention.

FIG. 2 illustrates a lyophilized biotherapeutic within an unsealed consumer package.

FIG. 3 illustrates the consumer package of FIG. 2 containing a lyophilized biotherapeutic sealed against outside contamination.

FIG. 4 illustrates subjecting the sealed consumer package of FIG. 3 containing a lyophilized biotherapeutic to microwave energy to attenuate viruses contained within the biotherapeutic.

FIG. 5 illustrates a plurality of sealed consumer packages containing lyophilized biotherapeutics ready to receive microwave energy.

FIG. 6 schematically illustrates a virus including a nucleic acid core, capsid envelope and water molecules.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
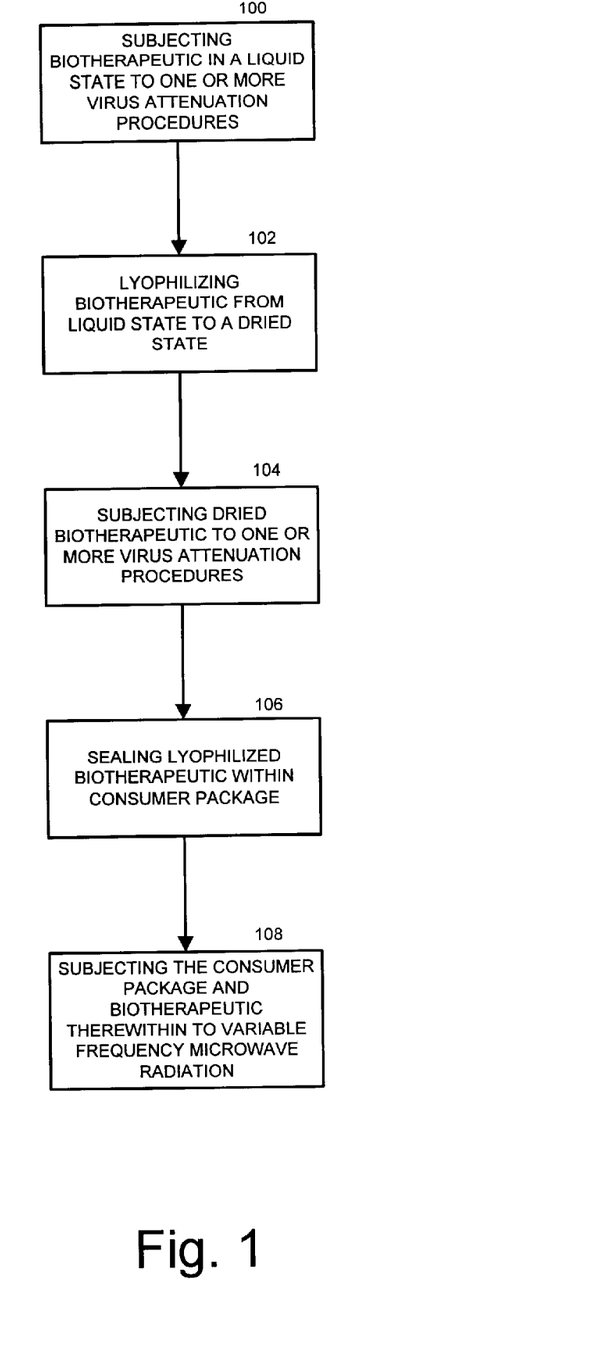

Referring now to FIG. 1, operations for attenuating viruses contained within biotherapeutics, according to the present invention, are schematically illustrated. The starting material for the manufacture of a biotherapeutic is most often a liquid (e.g., blood plasma, cell culture supernatant fraction, cell extract, plant extract). In the initial liquid state, a biotherapeutic may be screened for the presence of pathogens including viruses, but the success of this process may depend on knowledge of the pathogen. Subsequent manufacturing processes, such as precipitation and chromatographic fractionation may result in partitioning of viruses and other pathogens. Viral attenuation techniques (Block 100) such as filtration, heat treatment, chemical treatment and photodynamic treatment may be utilized at various points in a manufacturing process.

After a screening or attenuation process, the biotherapeutic is lyophilized from a liquid state to a dried state (Block 102). The lyophilized biotherapeutic may then be subjected to heat treatment, or other viral attenuation methods, to attenuate viruses contained therein (Block 104). The lyophilized biotherapeutic is then sealed within a container (referred to as a "consumer package") (Block 106). The consumer package and biotherapeutic therewithin are then subjected to microwave energy to attenuate any viruses, known or unknown, remaining within the biotherapeutic (Block 108). Each of these steps will be discussed below.

Subjecting Biotherapeutic in Liquid State to Conventional Virus Attenuation Method(s)

A biotherapeutic, such as blood plasma and other blood products, is typically prepared in a liquid state. Preferably conventional virus attenuation procedures are performed on a biotherapeutic while still in a liquid state (Block 100). Exemplary conventional virus attenuation methods include, but are not limited to, filtration, chemical treatment, heat treatment, photodynamic treatment, or combinations thereof. Many viruses can be removed or inactivated via these conventional attenuation techniques without causing harm to the biotherapeutic.

Drying the Virus-Attenuated Biotherapeutic from a Liquid State to a Dried State After being treated with one or more conventional virus attenuation methods, the biotherapeutic in the liquid state is then dried prior to being sealed within a consumer package (Block 102). A particularly preferred method of drying biotherapeutics is via a process known as "lyophilization". Lyophilization is a drying technique wherein a wet substance is frozen. Then, the solid moisture (ice) is allowed to sublime directly to vapor, bypassing its liquid form, by exposing it to vacuum. Lyophilization techniques are well known in the art of food processing and pharmaceutical manufacturing, and need not be described further herein. Preferably, biotherapeutics are lyophilized to a moisture content of no more than about one to two percent (1–2%) water content. However, lyophilized biotherapeutics containing up to two percent (2%) water content may be subjected to variable frequency microwave energy according to the present invention.

As is known to those skilled in the art of lyophilization, lyophilized biotherapeutics are advantageous because of ease of handling and storage. Furthermore, shelf life of a biotherapeutic in a lyophilized state may be longer and more stable than in a liquid state.

A dried biotherapeutic may then be subjected to one or more virus attenuation methods, such as heat treatment (Block 104), prior to being sealed within a container (Block 106).

Sealing Lyophilized Biotherapeutic within a Microwave Permeable Container

Figure 2:
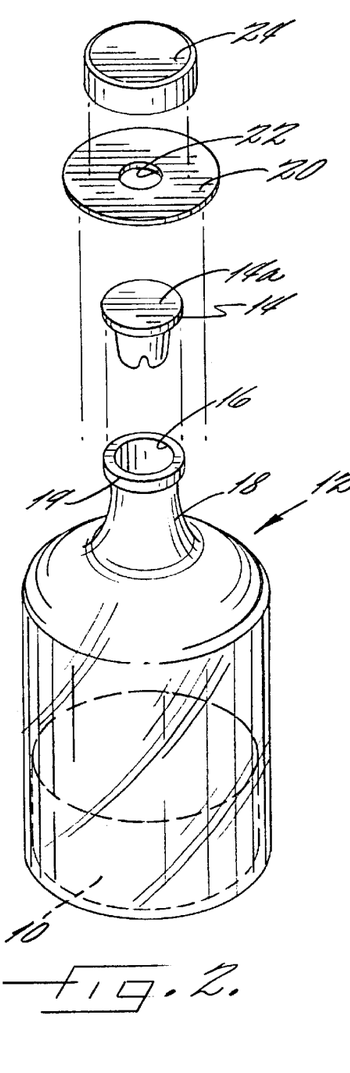
Figure 3:
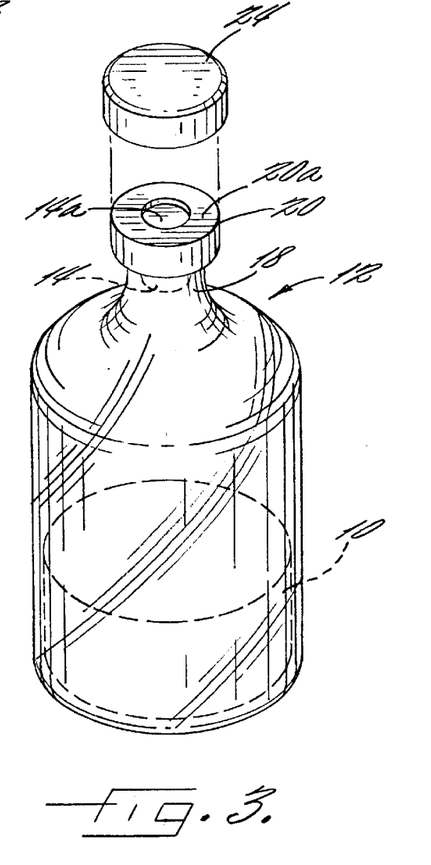

Referring now to FIGS. 2 and 3, a dried or lyophilized biotherapeutic 10 is contained within a container or consumer package 12. The term "consumer package" is intended to include all types of containers in which biotherapeutics can be delivered to end users, including, but not limited to, patients, medical care providers, hospitals, and the like. Preferably, the illustrated consumer package 12 of FIGS. 2 and 3 is a bottle formed of glass or other microwave permeable material that can be hermetically sealed. As will be discussed below, the present invention allows microwave energy to be successfully applied to a biotherapeutic even though portions of consumer packages are non-microwave permeable and/or contain conductive material.

A stopper 14 is configured to be inserted within an opening 16 in the neck 18 of the illustrated consumer package 12 to thereby seal the contained biotherapeutic 10 from external environments. A retaining member, 20 is configured to overlie the stopper upper surface 14a and be formed around a circumferential lip 19 of the neck 18 to securely retain the stopper 14 within the aperture 16. The retaining member 20 may be formed from a conductive material such as aluminum.

An aperture 22, formed in the retaining member 20, permits a needle or other device to be inserted through the stopper upper surface 14a and into the consumer package 12 to access the biotherapeutic 10. In the illustrated embodiment, a protective cap 24 is configured to overlie the upper portion 20a of the retaining member 20 to cover the stopper upper surface 14a and thereby prevent unwanted intrusion into the consumer package 12 therethrough.

Figure 4:
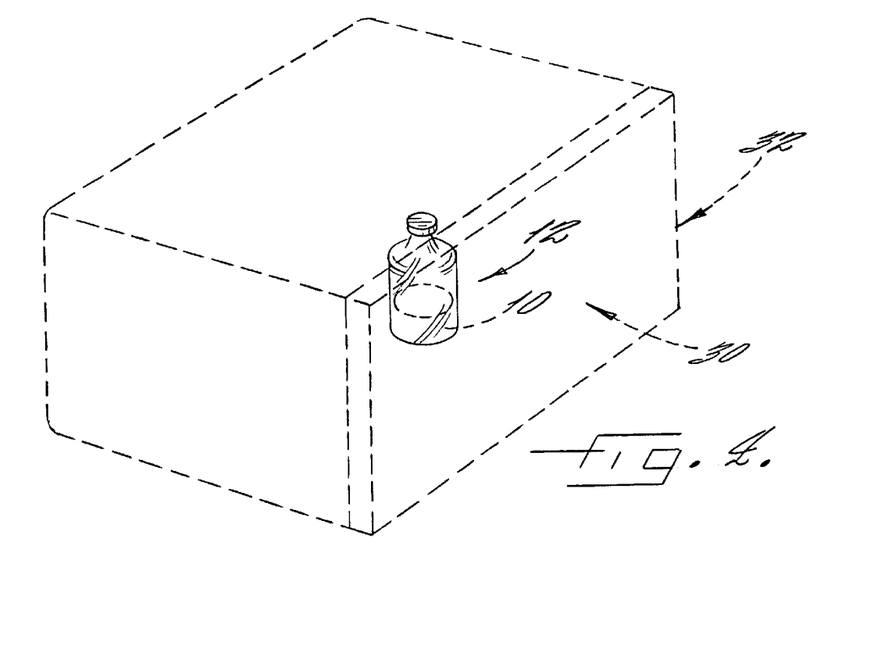

Subjecting Consumer Package and Biotherapeutic Contained Therewithin to Microwave Energy to Attenuate Viruses within the Biotherapeutic Referring now to FIG. 4, the consumer package 12 and biotherapeutic 10 contained therewithin, are positioned within a cavity 30 of a microwave furnace 32 in order to be subjected to variable frequency microwave energy (Block 108). Variable frequency microwave energy, or a combination of single and variable frequency microwave energy, may be utilized in accordance with the present invention. Preferably, microwave energy is applied to the biotherapeutic by sweeping the consumer package 12 and biotherapeutic 10 therewithin with at least one range of microwave frequencies to attenuate viruses remaining within the biotherapeutic 10.

An exemplary microwave furnace for carrying out the present invention is described in U.S. Pat. No. 5,321,222, to Bible et al., the disclosure of which is incorporated herein by reference in its entirety. Particularly preferred microwave furnaces for carrying out the present invention are a Micro-Cure 2100 batch furnace, a MicroCure 5100 in-line furnace, and a VariWave 1500 table top furnace, all manufactured by Lambda Technologies, Morrisville, N.C. In general, a microwave furnace for carrying out the present invention typically includes a microwave signal generator or microwave voltage-controlled oscillator for generating a low-power (i.e., between about 0.015 and 0.15 millivolts) microwave signal for input to the microwave furnace. A first amplifier may be provided to amplify the magnitude of the signal output from the microwave signal generator or the microwave voltage-controlled oscillator. A second amplifier may be provided for processing the signal output by the first amplifier.

A power supply may be provided for operation of the second amplifier. A directional coupler may be provided for detecting the direction of a signal and further directing the signal depending on the detected direction. Preferably a high-power broadband amplifier, such as, but not limited to, a traveling wave tube (TWT), tunable magnetron, tunable klystron, tunable twystron, and a tunable gyrotron, is used to sweep a range of frequencies of up to an octave in bandwidth and spanning a spectrum of from about 300 MHz to about 300 GHz. A range of microwave frequencies for attenuating viruses within a biotherapeutic, in accordance with the present invention, may include virtually any number of frequencies, and is not limited in size.

Use of variable frequency microwave processing, as disclosed herein, enhances uniform biotherapeutic processing from one consumer package to the next because placement of each consumer package within a microwave furnace cavity is not critical. By contrast, with single frequency microwave processing, each consumer package may need to be oriented the same way within the furnace cavity to achieve identical and repeatable virus attenuation processing time and quality. This is because single frequency microwave processing creates hot spots within a cavity that may overheat particular areas without heating other areas.

The practical range of frequencies within the electromagnetic spectrum from which microwave frequencies may be chosen is generally about 0.90 GHz to 90 GHz. Every biotherapeutic typically has at least one range of microwave frequencies that is optimum for attenuating viruses contained therewithin without damaging the biotherapeutic or the consumer package. Furthermore, the use of variable frequency microwave energy allows consumer packages containing conductive material to be subjected to microwave energy without arcing or causing other damage in the presence of package components which could arc or be damaged by single frequency microwave energy. Each range of microwave frequencies preferably has a central frequency that is optimum for attenuating a specific virus. The central frequency of each range is bounded on one end by a specific frequency and bounded on an opposite end by a different specific frequency.

Damage from arcing can occur when microwave energy is applied to conductive materials. However, arcing typically occurs only within certain ranges of microwave frequencies. Other ranges of microwave frequencies typically exist wherein arcing does not occur. By selecting one or more ranges of damage-free frequencies, virus attenuation can be performed on biotherapeutics using microwave energy without concern for damage from arcing, even where consumer packages contain conductive materials. Furthermore, a sweeping rate in a particular range of frequencies may also be selected to avoid damage to a consumer package and/or a biotherapeutic contained therewithin.

Each range of microwave frequencies preferably has a central frequency that is selected to rapidly perform virus attenuation. As will be described below, this means that the selected frequency offers the best match and is likely to be the frequency at which the nucleic acid of a virus or some component (or components) of a virus, in whole or in part, is at or near maximum absorption of microwave energy (microwave coupling). Microwave energy couples at the molecular level with the material to which it is applied producing volumetric electromagnetic and thermal energy distribution within the material.

The term "coupling" means the process by which energy is provided as microwave radiation is coupled or otherwise transferred to molecular components in a virus including, but not limited to, water, capsid protein and viral nucleic acid. Energy may be directly transferred to these molecular components by various known mechanisms including, but not limited to, excitation of molecular vibration via generation of harmonic acoustic vibration. Energy may be indirectly transferred to these molecular components by various known mechanisms including, but not limited to, excitation of a molecular component via another molecular component. An example of indirect transfer of energy is the excitation of water associated with a nucleic acid, protein, or both, via chemical bonds including, but not limited to, hydrogen bonds. Water associated with a nucleic acid, protein, or both, then transfers energy to the protein, nucleic acid, or both via conductive heat transfer mechanisms.

When microwave energy is optimally tuned for attenuating a virus at a central frequency within a range of frequencies, the attenuation is very efficient as compared with conventional convection heat ovens and can be preferential to a virus over other molecular structures. The extent to which a given virus absorbs microwave energy is determined by the applied microwave frequency, and the electric field distribution within the material.

Often there are multiple ranges of frequencies within which virus attenuation may occur without causing damage to a biotherapeutic or consumer package. For example, a virus may be attenuated without causing damage between 3.50 GHz and 6.0 GHz, and may also be attenuated without causing damage between 7.0 GHz and 10.0 GHz. The availability of additional ranges provides additional flexibility for achieving rapid, uniform, yet damage-free virus attenuation. The availability of alternative ranges permits a virus to be attenuated with microwave energy without having to resort to other attenuation methods. The availability of multiple ranges of frequencies also permits "hopping" between two or more ranges during microwave processing to obtain optimum attenuation. For example, optimum attenuation of a particular virus may be obtained by sweeping with microwave frequencies between 3.50 GHz and 6.0 GHz for a period of time and then sweeping, for a period of time, between 7.0 GHz and 10.0 GHz. Hopping may also be advantageous for treating multiple viruses at the same time. For example, one range may be optimum for treating one virus and another range may be optimum for treating another virus.

Preferably, frequency sweeping is performed using frequencies from within at least one range of frequencies, as described above. Frequency sweeping facilitates uniform virus attenuation because many cavity modes can be excited. Frequency sweeping may be accomplished by launching the different frequencies within a range either simultaneously, or sequentially. For example, assume a range of frequencies is 2.60 GHz to 7.0 GHz. Frequency sweeping would involve continuously and/or selectively launching frequencies within this range in any desirable increments, such as 2.6001 GHz, 2.6002 GHZ, 2.6003 GHz . . . 3.30 GHz, etc. Virtually any incremental launching pattern may be used without departing from the spirit and intent of the present invention.

The rate at which the different frequencies are launched is referred to as the sweep rate. This rate may be any value, including, but not limited to, milliseconds, and minutes. Preferably, a sweep rate is as rapid as practical. In addition, a sweep rate may be selected so that an optimum number of modes are generated within a microwave furnace cavity. Sweep rate may also be selected based on the virus or viruses to be attenuated.

Figure 5:
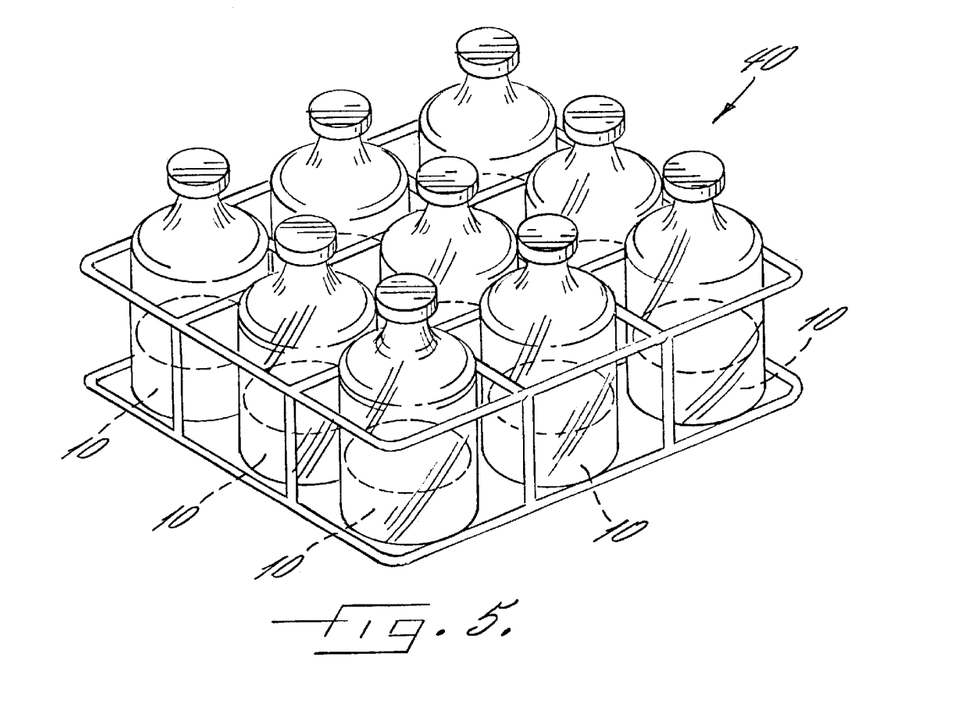

The uniformity in virus attenuation afforded by frequency sweeping provides flexibility in how consumer packages are oriented within a microwave furnace, and permits a plurality of consumer packages 40 (FIG. 5), each containing lyophilized biotherapeutics 10, to be processed at the same time. Maintaining each consumer package in precisely the same orientation is not required to achieve uniform virus attenuation. Furthermore, the variable frequency sweeping method of attenuating viruses in biotherapeutics, according to the present invention, can be applied in both single mode and multi-mode microwave cavities.

Preferably, a variable frequency microwave furnace for attenuating viruses, according to the present invention, is under computer control. Under computer control, a microwave furnace may be tuned to a particular frequency, preferably an optimum incident frequency for a particular biotherapeutic and virus, and then may be programmed to sweep around this central frequency to generate a plurality of modes and rapidly move them around the cavity to provide a uniform energy distribution. In addition, an optimum coupling frequency may change during the processing of a biotherapeutic sample. Accordingly, it is preferred that a central frequency be adjustable, preferably under computer control, to compensate automatically for such changes.

Theories of Viral Attenuation Via Microwave Enerqy

Figure 6:
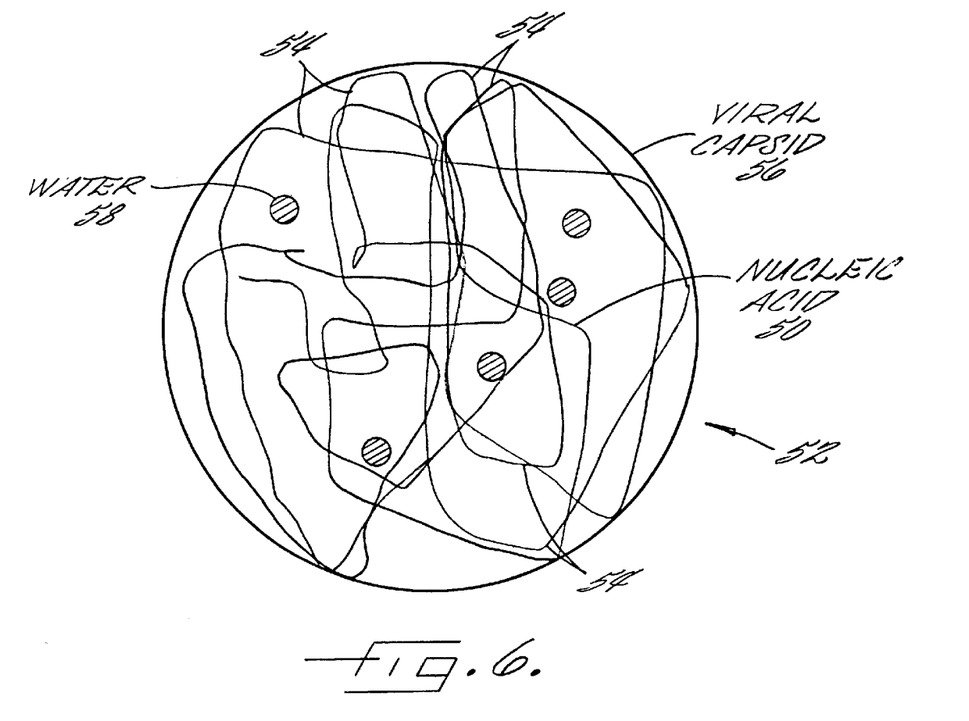

Although not fully understood, Applicants believe that there are at least three theories that explain how microwave energy attenuates a virus within a biotherapeutic according to the present invention. Referring to FIG. 6, each of these theories centers around the presumption that a nucleic acid core 50 of a virus 52 is disrupted or broken in some manner, or that the association of nucleic acid and capsid and/or relation between capsid components is disrupted. As is known to those skilled in the art of nucleic acids, nucleic acids, such as ribonucleic acid (RNA) and deoxyribonucleic acid (DNA) are large, acidic, chainlike molecules having a helix structure. The helix structure is composed of a strand 54 of material such as purine and pyrimidine joined together by hydrogen bonds.

According to one theory, microwave energy causes vibrations within the helix of the nucleic acid that can cause a helix strand 54 to break apart. According to another theory, the capsid 56 enclosing the nucleic acid core 50 of a virus 52 is modified by microwave energy such that the virus 52 itself can lose its ability to infect living cells. For example, microwave energy can affect the envelope surrounding a virus such that the virus cannot attach itself to another cell. Alternatively, microwave energy may disrupt an association of nucleic acid and capsid necessary for infectivity.

According to a third theory, it is well known that there are water molecules 58 in close association with the nucleic acid core 50 of a virus 52 inside the capsid 56. Water molecules are also in association with capsomers, and there is also mediating association of nucleic acid and capsid. When a biotherapeutic has been lyophilized (i.e., only approximately 1%–2% water content), it is possible that selective coupling with water molecules 58 inside the viral capsid 56 via microwave energy can result in inactivation of the virus.

Water molecules are believed to provide stability to the nucleic acid and capsids of a virus. By coupling with the water molecules, the nucleic acid, the capsid, and the interaction between the nucleic acid and capsid can become unstable rendering the virus ineffective.

Residual protein activity of at least seventy percent (70%) and a virus reduction of four logs are desirable.

EXAMPLE 1

A VFM model 1500 (6–18 GHz) microwave furnace was used to expose select biotherapeutics (intravenous immunoglobulin, blood coagulation factor VIII, fibrinogen and prothrombin complex concentrates) to variable frequency microwaves. These protein biotherapeutics were all dried (lyophilized) product. The bottles containing these biotherapeutics were placed inside the furnace cavity and a thermal probe was inserted through the septum (rubber stopper 14 FIG. 2) to measure product temperature. Temperature measurements were made internally (i.e., the temperature of the biotherapeutic within a bottle) with the thermal probe and externally (i.e., the temperature outside of a bottle within the furnace cavity) with a fiberoptic probe. Variable frequency microwave exposure was performed at 10 GHz with a 0.7 GHz bandwidth and a 0.1 second sweep rate. Table 1 displays time and average maximum temperature reached for the selected biotherapeutics.

TABLE 1

| Protein Biotherapeutic | Time (min.) | Avg. Max External Temp. (° C.) | Avg. Max Internal Temp. (° C.) | Protein Analysis after Exposure |
|---|---|---|---|---|
| Empty | 2 | 49 | 56 | — |
| Empty | 5 | 77 | 81 | — |
| Empty | 10 | 96 | 97 | — |
| Intravenous immunoglobulin | 2 | 49 | 49 | 99.9* |
| Intravenous immunoglobulin | 5 | 73 | 85 | 98.0* |
| Blood coagulation factor VIII | | 81 | 93 | 92.3** |
| Blood coagulation factor VIII | | 99 | 102 | 91.0** |
| Anti-inhibitor coagulant complex | | 75 | 80 | ND |
| Anti-inhibitor coagulant complex | | 97 | 96 | ND |
| Factor IX complex | | 75 | 79 | ND |
| Factor IX complex | | 99 | 96 | ND |
| Fibrinogen | | 79 | 93 | 121.7*** |
| Fibrinogen | | 105 | 116 | 89.8*** |

*Intravenous immunoglobulin analysis was performed through HPLC. The protein analysis was calculated as follows:

$$\text{Protein Analysis} = \frac{100 * \text{Percent Monomer}_f}{\text{Percent Monomer}_i}$$

Where Percent Monomer$_f$ is after microwave processing and Percent Monomer$_i$ is taken from a control.
**Factor VIII analysis was measured as a potency (IU/mL) and then calculated into a Percent of Reference. The control is 96.8% and anything between 80 and 120% is within norm.
***Fibrinogen was measured as FXIII activity in u/mL and then calculated as follows:

TABLE 1-continued

| Protein Biotherapeutic | Time (min.) | Avg. Max External Temp. (° C.) | Avg. Max Internal Temp. (° C.) | Protein Analysis after Exposure |
|---|---|---|---|---|

$$\text{Protein Analysis} = \frac{100 * \text{Factor XIII activity}_f}{\text{Factor XIII activity}_I}$$

Where Factor XIII activity$_f$ is after microwave processing and Factor XIII$_I$ is taken from a control.

The temperature measurements in Table 1 represent bulk energy transfer to each bottle and contents thereof, which mostly include a biotherapeutic and excipients, via microwave energy and are not necessarily believed to measure energy transferred to a virus or viral components. These bulk temperature measurements are a convenient index of product stability and are not meant to suggest a necessary relation to viral attenuation.

The integrity of the protein biotherapeutics after microwave exposure was analyzed in regards to biological activity and other characteristics. The data in Table 1 demonstrates that there was no significant loss of activity in Factor VIII preparations or topical Fibrinogen complex.

EXAMPLE 2

Biotherapeutics were exposed to ranges of ave frequencies with central frequencies of 8, 10, 12 and 17.5 GHz with 0.7 GHz bandwidths to determine whether there was a frequency effect on the biotherapeutics. Temperature measurements were made internally with a thermal probe and externally with a fiberoptic probe. The data for Factor VIII is summarized below in Table 2.

TABLE 2

| Frequency (GHz) | Time (min.) | Emp. External Max Temp. (° C.) | Emp. Internal Max Temp. (° C.) | Factor VIII External Max Temp. (° C.) | Factor VIII Internal Max Temp. (° C.) | Factor VIII Activity (u/mL) |
|---|---|---|---|---|---|---|
| Control | — | — | — | — | — | 112.4 |
| 8 | 5 | 99 | 92 | 94 | 87 | 101.4 |
| 8 | 10 | 117 | 94 | 114 | 102 | 48.7* |
| 10 | 5 | 66 | 67 | 94 | 78 | 101.2 |
| 10 | 10 | 82 | 79 | 89 | 84 | 98.7 |
| 12 | 5 | 68 | 69 | 82 | 81 | 98.7 |
| 12 | 10 | 84 | 77 | 100 | 95 | 92.3 |
| 17.5 | 5 | 68 | 57 | 75 | 79 | 104.5 |
| 17.5 | 10 | 76 | 71 | 90 | 85 | 103.5 |

*This temperature excursion is too high for the protein to retain much activity.

Table 2 illustrates that biotherapeutics can be exposed to different microwave frequencies without being harmed under the stated conditions which result in the indicated temperature measurements.

EXAMPLE 3

To determine whether inactivation of viruses is achievable, 8 log (10) units (as defined in a standardized cytotoxicity assay) of Porcine Parvovirus was spiked into samples of Topical Fibrinogen. Table 3 summarizes the kill (attenuation) after variable frequency microwave exposure for both 5 and 10 minutes at 8, 10, 12, 14 and 17.5 GHz.

TABLE 3

| Frequency (GHz) | Time (Min.) | Sample 1 RF (log10) | Sample 2 RF (log10) |
|---|---|---|---|
| 8 | 5 | 0.43 | 1.9 |
| 8 | 10 | 3.93 | 3.94 |
| 10 | 5 | 0.33 | 0.53 |
| 10 | 10 | 4.73 | 4.73 |
| 12 | 5 | 0.83 | 0.53 |
| 12 | 10 | 2.63 | 2.99 |
| 14 | 5 | 0.23 | |
| 14 | 10 | 1.33 | |
| 17.5 | 5 | 0.93 | 0.93 |

The kill at 10 GHz and 10 minutes is over 4 logs and means a 58,000 reduction in active virus. This is an adequate level of virus reduction to meet both United States Food and Drug Administration requirements and European Regulatory requirements. There are no other current techniques which can reduce Parvovirus with retention of activity of a biotherapeutic.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of attenuating a virus contained within a dried biotherapeutic sealed within a container without harming the biotherapeutic and without exposing the biotherapeutic to additional viruses, comprising sweeping the container and biotherapeutic therewithin with at least one range of microwave frequencies that preferentially excites nucleic acid molecules of the virus such that cores of the nucleic acid molecules are disrupted.

2. A method according to claim 1 wherein the at least one range of microwave frequencies is a plurality of ranges of microwave frequencies.

3. A method according to claim 1 wherein the at least one range of microwave frequencies has a central frequency selected to disrupt a helix strand of a nucleic acid of the virus without harming the biotherapeutic.

4. A method according to claim 1 wherein the at least one range of microwave frequencies has a central frequency selected to modify a capsid enclosing a nucleic acid of the virus without harming the biotherapeutic.

5. A method according to claim 1 wherein the at least one range of microwave frequencies has a central frequency selected to selectively couple with water molecules inside a capsid enclosing a nucleic acid of the virus to disrupt the nucleic acid without harming the biotherapeutic.

6. A method according to claim 1 wherein the biotherapeutic is infected with a virus selected from the group consisting of parvovirus, hepatitis A, ribonucleic acid virus, and deoxyribonucleic acid virus.

7. A method according to claim 1 wherein the biotherapeutic is derived from the group consisting of human blood, fractionation of a cell culture supernatant, fractionation of a fermentation supernatant, fractionation of a cell extract, fractionation of milk from a transgenic animal, and fractionation of a plant extract.

8. A method of uniformly attenuating a virus contained within dried biotherapeutic sealed within a plurality of containers without harming the biotherapeutic and without exposing the biotherapeutic to additional viruses, the method comprising:

inserting the plurality of containers within a microwave furnace cavity; and sweeping the plurality of containers and biotherapeutic contained therewithin with at least one range of microwave frequencies that preferentially excites nucleic acid molecules of the virus such that cores of the nucleic acid molecules are disrupted.

9. A method according to claim 8 wherein the at least one range of microwave frequencies is a plurality of ranges of microwave frequencies.

10. A method according to claim 8 wherein the at least one range of microwave frequencies has a central frequency selected to disrupt a helix strand of a nucleic acid of the virus without harming the biotherapeutic.

11. A method according to claim 8 wherein the at least one range of microwave frequencies has a central frequency selected to modify a capsid enclosing a nucleic acid of the virus without harming the biotherapeutic.

12. A method according to claim 8 wherein the at least one range of microwave frequencies has a central frequency selected to selectively couple with water molecules inside a capsid enclosing a nucleic acid of the virus to disrupt the nucleic acid without harming the biotherapeutic.

13. A method according to claim 8 wherein the biotherapeutic is infected with a virus selected from the group consisting of parvovirus, hepatitis A, ribonucleic acid virus, and deoxyribonucleic acid virus.

14. A method according to claim 8 wherein the biotherapeutic is derived from the group consisting of human blood, fractionation of a cell culture supernatant, fractionation of a fermentation supernatant, fractionation of a cell extract, fractionation of milk from a transgenic animal, and fractionation of a plant extract.

15. A method of preparing a virus-free biotherapeutic, comprising the steps of:

drying a biotherapeutic from a liquid state to a dried state;

sealing the dried biotherapeutic within a container; and sweeping the container and biotherapeutic therewithin with at least one range of microwave frequencies selected to attenuate known and unknown viruses contained within the biotherapeutic by preferentially exciting nucleic acid molecules of the known and unknown viruses such that cores of the nucleic acid molecules of the known and unknown viruses are disrupted.

16. A method according to claim 15 wherein the drying step is performed by lyophilization.

17. A method according to claim 15 further comprising the step of subjecting the biotherapeutic to a virus attenuation process prior to the drying step.

18. A method according to claim 17 wherein the virus attenuation process is selected from the group consisting of filtration, chemical treatment, heat treatment, and photodynamic treatment.

19. A method according to claim 15 wherein the at least one range of microwave frequencies is a plurality of ranges of microwave frequencies.

20. A method according to claim 15 wherein the at least one range of microwave frequencies has a central frequency selected to disrupt a helix strand of a nucleic acid of the virus without harming the biotherapeutic.

21. A method according to claim 15 wherein the at least one range of microwave frequencies has a central frequency selected to modify a capsid enclosing a nucleic acid of the virus without harming the biotherapeutic.

22. A method according to claim 15 wherein the at least one range of microwave frequencies has a central frequency selected to selectively couple with water molecules inside a capsid enclosing a nucleic acid of the virus to disrupt the nucleic acid without harming the biotherapeutic.

23. A method according to claim 15 wherein the biotherapeutic is infected with a virus selected from the group consisting of parvovirus, hepatitis A, ribonucleic acid virus, and deoxyribonucleic acid.

24. A method according to claim 15 wherein the biotherapeutic is derived from the group consisting of human blood, fractionation of a cell culture supernatant, fractionation of a fermentation supernatant, fractionation of a cell extract, fractionation of milk from a transgenic animal, and fractionation of a plant extract.

25. A method of preparing a virus-free biotherapeutic, comprising the steps of:

subjecting a biotherapeutic in a liquid state to a virus attenuation process, wherein the biotherapeutic is derived from the group consisting of human blood, fractionation of a cell culture supernatant, fractionation of a fermentation supernatant, fractionation of a cell extract, fractionation of milk from a transgenic animal, and fractionation of a plant extract, and wherein the biotherapeutic is infected with a virus selected from the group consisting of parvovirus, hepatitis A, ribonucleic acid virus, and deoxyribonucleic acid virus;

lyophilizing the virus attenuated biotherapeutic from a liquid state to a dried state;

sealing the dried biotherapeutic within a microwave permeable container; and sweeping the container and biotherapeutic therewithin with at least one range of microwave frequencies to attenuate viruses remaining within the biotherapeutic without damaging the biotherapeutic or the container by preferentially exciting nucleic acid molecules of the viruses remaining in the container such that cores of the nucleic acid molecules are disrupted.

26. A method according to claim 25 wherein the virus attenuation process prior to the lyophilizing step is selected from the group consisting of filtration, chemical treatment, heat treatment, and photodynamic treatment.

27. A method according to claim 25 further comprising the step of subjecting the dried biotherapeutic to a virus attenuation process prior to the step of sealing the dried biotherapeutic within a microwave permeable container.

28. A method according to claim 25 wherein the at least one range of microwave frequencies is a plurality of ranges of microwave frequencies.

29. A method according to claim 25 wherein the at least one range of microwave frequencies has a central frequency selected to disrupt a helix strand of a nucleic acid of the virus without harming the biotherapeutic.

30. A method according to claim 25 wherein the at least one range of microwave frequencies has a central frequency selected to modify a capsid enclosing a nucleic acid of the virus without harming the biotherapeutic.

31. A method according to claim 25 wherein the at least one range of microwave frequencies has a central frequency selected to selectively couple with water molecules inside a capsid enclosing a nucleic acid of the virus to disrupt the nucleic acid without harming the biotherapeutic.

* * * * *